(12) United States Patent
Ogawa et al.

(10) Patent No.: US 6,451,799 B1
(45) Date of Patent: Sep. 17, 2002

(54) DRUGS FOR AMELIORATING OCULAR CIRCULATORY DISORDERS

(75) Inventors: Takahiro Ogawa, Nishinomiya (JP); Noriko Watanabe, Suita (JP); Mitsunori Waki, Kobe (JP)

(73) Assignees: Senju Pharmaceutical Co., Ltd., Osaka (JP); Kyoto Pharmaceutical Industries, Ltd., Kyoto (JP)

( * ) Notice: Subject to any disclaimer, the term of this patent is extended or adjusted under 35 U.S.C. 154(b) by 0 days.

(21) Appl. No.: 09/297,197

(22) PCT Filed: Oct. 23, 1997

(86) PCT No.: PCT/JP97/03866

§ 371 (c)(1), (2), (4) Date: Apr. 27, 1999

(87) PCT Pub. No.: WO98/18471

PCT Pub. Date: May 7, 1998

(30) Foreign Application Priority Data

Oct. 28, 1996 (JP) .............................................. 8-285684
Sep. 10, 1997 (JP) .............................................. 9-245559

(51) Int. Cl.$^7$ .............................................. A61K 31/50
(52) U.S. Cl. .................. 514/252.13; 514/912; 514/913
(58) Field of Search ........................... 514/218, 252.13, 514/341, 913, 912

(56) References Cited

U.S. PATENT DOCUMENTS 4,937,242 A * 6/1990 Matsui et al. ............. 514/235.8
5,435,998 A * 7/1995 Abelson ..................... 514/912

FOREIGN PATENT DOCUMENTS

| JP | 63-225355 | 9/1988 |
| JP | 3-145464 | 6/1991 |
| JP | 8-506807 | 7/1996 |

OTHER PUBLICATIONS

Akira Sawada et al., "Prevention of Visual Field Defect Progression with Brovincamine in Eyes with Normal-tension Glaucoma", Ophthalmology, vol. 103, No. 2, pp. 283–288, Feb. 1996.

Yoshiaki Kitazawa et al., "The effect of Ca$^{2+}$-antagonist on visual field in low-tension glaucoma", Graefe's Arch Clin. Exp. Ophthalmol, 227, pp. 408–412, 1989.

Peter A. Netland et al., "Calcium Channel Blockers in the Managment of Low-tension and Open-angle Glaucoma", American Journal of Ophthalmology, vol. 115, No. 5, pp. 608–613, May 1993.

Seiyo Harino et al., "Intravenous Nicardipine in Cats Increases Optic Nerve Head but not Retinal Blood Flow", Investigative Ophthalmology & Visual Science, vol. 33, No. 10, pp. 2885–2890, Sep. 1992.

The Merck Manual of Medical Information—Home Edition, Section 20, Eye Disorders, Chapter 226, (3 pages).

* cited by examiner

*Primary Examiner*—Zohreh Fay
(74) *Attorney, Agent, or Firm*—Wenderoth, Lind & Ponack, L.L.P.

(57) ABSTRACT

An agent for ameliorating ocular circulatory disorder containing a 1,4-dihydropyridine derivative of the formula (I)

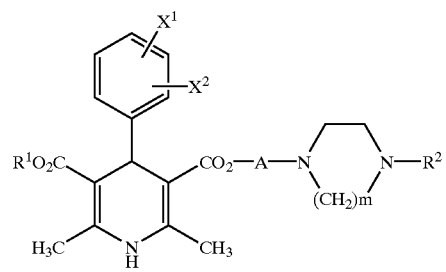

wherein each symbol is as defined in the specification, or an acid addition salt thereof as an active ingredient. The agent for ameliorating ocular circulatory disorder containing the compound of the above formula (I) increases optic disc blood flow of normal eye particularly by instillation, and inhibits vasocontraction of retinal blood vessel, decrease in optic disc blood flow and attenuation of the amplitude of VEP caused by ET-1, without increasing the intraocular pressure. Therefore, the inventive compound is suggested to be effective as a therapeutic agent against, from among the types of glaucoma, particularly normal tension glaucoma caused by ocular circulation disorder and retinitis pigmentosa, macular degeneration, ischemic optic neuropathy, iridocyclitis, retinal artery occlusion, retinal vein occlusion, diabetic retinopathy, ischemic optic neuropathy, retinochoroidal disease following choroidal lesion, retinochoroidal disease associated with systemic disease, and the like.

13 Claims, 9 Drawing Sheets

Time (min) after injection of ET-1

DRUGS FOR AMELIORATING OCULAR CIRCULATORY DISORDERS

This application is a 371 of PCT/JP97/03866 filed Oct. 23, 1997.

TECHNICAL FIELD

The present invention relates to an agent for ameliorating ocular circulatory disorder. More particularly, the present invention relates to an agent for ameliorating ocular circulatory disorder, comprising a specific 1,4-dihydropyridine derivative or an acid addition salt thereof as an active ingredient.

BACKGROUND ART

An intraocular blood circulation hereinafter to be referred to as ocular circulation) has two major pathways, one being a circulation via ciliary artery and the other being a circulation via central retinal artery. The ciliary artery is connected to the arteries of choroid, optic disc, iris, ciliary body and the like, and the blood is discharged from the eye through the vortex vein. The central retinal artery passes through optic nerve and is connected to the central retinal vein, wherein a part thereof is branched into arteriola at the optic disc and then into capillary. Of these, the circulatory disorder of ciliary artery includes normal tension glaucoma, retinitis pigmentosa, macular degeneration, ischemic optic neuropathy, iridocyclitis and the like. The circulatory disorder of the central retinal artery includes retinal artery occlusion, retinal vein occlusion, diabetic retinopathy, ischemic optic neuropathy, choroidal disease following retinal lesion, retinochoroidal disease associated with systemic disease and the like. As is evident from the description of the above-mentioned ocular circulation pathway, the diseases caused by the above-mentioned ocular circulation disorders make an onset when the smooth circulation of retina, optic disc, choroid, iris, diary body and the like is prevented.

In recent years, there has been a high incidence of glaucoma, in particular, normal tension glaucoma (also referred to as low tension glaucoma) due to blood circulatory disorder in optic disc, and therapeutic method of the disease has been desired. By the epidemiological studies in recent years, normal tension glaucoma has been elucidated to be of a disease type of glaucoma having the highest incidence, though the intraocular pressure is in the normal range, so that it is considered to be distinct from the generally known glaucoma, namely the glaucoma caused by a high intraocular pressure. The normal tension glaucoma is generally considered to be a disease associated with (1) an intraocular pressure including a biological rhythm of not more than 21 mmHg, (2) a normal open angle, (3) glaucomatous optic disc cupping and the corresponding visual field disorder, (4) no intracranial lesion or paranasal sinuses disease which can cause optic atrophy and (5) no mass hemorrhage or shock [Low Tension Glaucoma and endotheline (ET-1), *Folia Ophthalmolgica Japonica*, vol. 43, pp. 554–559 (1992) and Low Tension Glaucoma—History and Concept, *Journal of the Eye*, vol. 8, pp. 493–500 (1991)).

A recent report has documented that an oral administration of a circulation ameliorating agent to a patient with normal tension glaucoma resulted in an increased optic disc blood flow and an ameliorated normal tension glaucoma [Influence of $Ca^{2+}$ antagonist on changes in visual field in low tension glaucoma, *Journal of Japanese Ophthalmological Society*, vol. 92, pp. 792–797 (1988)]. There is a possibility that various biological vasocontracting substances that decrease blood flow may be involved in patients with normal tension glaucoma, and a significantly higher endotheline-1 (hereinafter sometimes referred to as ET-1) concentration in blood as compared to the level in healthy subjects has been reported [(Low Tension Glaucoma and Endotheline (ET-1), *Folia Ophthalmolgica Japonica*, vol. 43, pp. 554–559 (1992)]. ET-1 is considered to act on a receptor present in vascular smooth muscle cells and directly opens the voltage-dependent $Ca^{2+}$ channel [intracellular Signal Transduction Pathway Relating to the Action and Regulation of Release of Endotheline, Experimental Medicine, vol. 8, pp. 28–35 (1990)].

Moreover, a decrease in optic disc blood flow by an injection of ET-1 into the vitreous body has been disclosed [Effect of Endotheline-1 on Ocular Circulation, *Journal of Japanese Ophthalmological Society*, vol. 97, pp. 678–682 (1993)]. A visual evoked potential (hereinafter also referred to as VEP) detects visual optic response of optic pathway from retinal ganglion cell to light, and can be one indication of visual field disorder. VEP shows attenuation of amplitude, disappearance of wave factor and prolonged peak latency due to disorders in retinal center and visual pathway. It has been disclosed that an injection of ET-1 results in attenuation of amplitude and prolonged peak latency [Changes in Visual Function by Injection into Endotheline Vitreous Body, *Journal of Japanese Ophthalmological Society*, vol. 97, pp. 467–473 (1993)]. From these, a possible involvement of various biological vasocontracting substances is suggested with respect to circulatory disorders in normal tension glaucoma, of which ET-1 is particularly plausible, wherein the possibility is suggested that ET-1 may cause an ocular circulation disorder, decrease optic disc blood flow and deteriorate visual function. Therefore, amelioration of an ocular circulation disorder induced by ET-1 is considered to be one of the effective therapeutic methods of normal tension glaucoma.

The ocular circulation disorder is most frequently seen among the retinochoroidal diseases. The retinochoroidal disease caused by an ocular circulation disorder is exemplified by retinal artery occlusion, retinal vein occlusion, diabetic retinopathy, retinitis pigmentosa, macular degeneration, choroidal disease following retinal lesion, retinochoroidal disease associated with systemic disease, and the lie. While the etiology of retinal artery occlusion and retinal vein occlusion is unknown, the lumen of retinal artery or vein is occluded to cause circulation disorder in retina and optic disc. In addition, the high ET-1 concentration in blood of a patient has been also reported [Deviation of Vasospasm Factor in Retinal Artery Occlusion, *Japanese Journal of Clinical Ophthalmology*, vol. 46, pp. 431–434 (1992)]. It is a well-known fact that thrombosis occurs in retinal blood vessel in diabetic retinopathy, which in turn causes retinal circulatory disorder. The retinitis pigmentosa is a binocular retinal disease, which starts with night blindness in school age, gradually progresses into abnormal visual field and visual loss, and may ultimately end in blindness. This disease is hereditary and the degeneration of retinal photo-receptor cell proceeds with increasingly narrower retinochoroidal blood vessel and circulatory disorders. An ocular circulation disorder is said to be observed in macular degeneration as well. The above-mentioned diseases that accompany ocular circulation disorder have been treated by an oral administration of tocopherol nicotinate (Juvela N : vitamin E preparation manufactured by EISAI CO., LTD.)

The optic nerve disease associated with an optic nerve disorder is exemplified by ischemic optic neuropathy and the like. The ischemic optic neuropathy gives an onset by circulatory disorder of optic nerve nutrient blood vessel. The disease accompanied by iris ciliary body circulatory disorder is exemplified by iridocyclitis and the like.

As the drug having peripheral vasodilating action, calcium antagonists representatively including nicardipine are known, which inhibit influx of Ca ion necessary for contraction of cardiac muscle and vascular smooth muscle, thereby relaxing the cardiac muscle and vascular smooth muscle and thus leading to vasodilation that increases the blood flow.

Japanese Patent Unexamined Publication No. 63-225355 discloses that certain 1,4-dihydropyridine derivative shows calcium antagonism, such as coronary arterial vasodilating action, cerebral vasodilating action, peripheral vasodilating action, intraocular smooth muscle relaxing action, renal vasodilating action and the like, thereby suggesting the usefulness thereof as a peripheral circulation ameliorating agent and for the prophylaxis and treatment of glaucoma However, Japanese Patent Unexamined Publication No. 63-225355 fails to disclose or suggest that the peripheral vasodilating action is expressed on retinochoroid and that the intraocular smooth muscle relaxing action is expressed on retinochoroid. It also fails to refer to the inhibition of contraction of blood vessel and decrease in blood flow, or suppression of attenuation of the amplitude of VEP by ET-1. Moreover, this reference does not disclose that this derivative is useful for the prophylaxis and treatment of the diseases caused by ocular circulation disorder such as glaucoma, particularly, normal tension glaucoma, and retinitis pigmentosa, macular degeneration, ischemic optic neuropathy, iridocyclitis, retinal artery occlusion, retinal vein occlusion, diabetic retinopathy, choroidal disease following retinal lesion, retinochoroidal disease accompanied by systemic disease and the like.

It has been also reported that the above-mentioned 1,4-dihydropyridine derivative increases blood flow in the brain, brown adipose tissue, small intestine, large intestine and skin of rat, but decreases blood flow in the liver, spleen, kidney, adrenal gland and skeletal muscle; that the decrease in blood flow by ET-1 can be suppressed in the kidney, adrenal gland, brown adipose tissue, small intestine, large intestine and skeletal muscle, but otherwise in the brain, lung and skin; and that the vasocontraction by ET-1 can be suppressed in the kidney, adrenal gland, brown adipose tissue, small intestine, large intestine and skeletal muscle but otherwise in the brain, lung and skin [Hypertens Res 17, 29–34 (1994)]. Therefore, while the above-mentioned blood flow increasing action of 1,4-dihydropyridine derivative and inhibition of the decrease in blood flow and vasocontraction by ET-1 are organ specific, there is no knowing if such action can be also found in retinochoroid.

DISCLOSURE OF THE INVENTION

The present invention aims at solving the above-mentioned problems and has been made with the purpose of providing an agent for ameliorating an ocular circulatory disorder, which has a superior blood flow increasing action in retinochoroid and which has an inhibitory action on the vasocontraction, decrease in blood flow and attenuation of the amplitude of VEP by ET-1 which is one of the biological vasocontracting substances.

The present inventors have conducted intensive studies in an attempt to achieve the above-mentioned objects and found that, from among the calcium antagonists, the above-mentioned 1,4-dihydropyridine derivative alone shows a superior blood flow increasing action in retinochoroid and an inhibitory action on vasocontraction, decrease in blood flow and attenuation of the amplitude of VEP by ET-1, and that, particularly in the form of an eye drop, the compound of the present invention does not increase intraocular pressure, though other 1,4-dihydropyridine derivatives reportedly do [nicardipine chloride (Effects of $Ca^{2+}$ Channel Blocker on Intraocular Pressure and Kinetics of Aqueous Humor of House Rabbits, *Journal of Japanese Ophthalmological Society*, 97, 665–671 (1993)].

Accordingly, the present invention provides the following.

(1) An agent for ameliorating an ocular circulatory disorder, comprising a 1,4-dihydropyridine derivative of the formula (I)

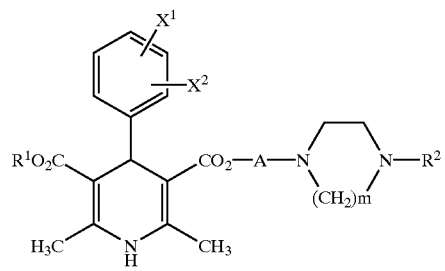

wherein $X^1$ and $X^2$ are the same or different and each is hydrogen atom, fluoromethyl, fluoromethoxy, halogen, cyano or nitro;

$R^1$ is lower alkyl;

$R^2$ is acyl, alkoxycarbonyl, acylalkyl, N-alkyl-substituted carbamoylalkyl, alkoxyalkyl, alkoxycarbonylalkyl, acyloxyalkyl, nitratoalkyl, cyanoalkyl, heterocyclic alkyl, haloalkyl, alkenyl or alkynyl;

A is alkylene having a carbon atom bonded with two alkyl and having a total number of carbon atoms of 5 or more; and m is an integer of 1 to 3, or an add addition salt as an active ingredient.

(2) The agent for ameliorating ocular circulatory disorder of (1) above, wherein, in the formula (I), $R^2$ is acylalkyl, N-alkyl-substituted carbamoylalkyl, alkoxyalkyl, cyanoalkyl, heterocyclic alkyl, haloalkyl, alkenyl or alkynyl.

(3) The agent for ameliorating ocular circulatory disorder of (1) above, wherein, in the formula (I), $R^2$ is alkenyl or alkynyl.

(4) The agent for ameliorating ocular circulatory disorder of (1) above, wherein, in the formula (I), A is alkylene having a carbon atom bonded with two alkyl and having a total number of carbon atoms of 5 to 10.

(5) The agent for ameliorating ocular circulatory disorder of any of (1) to (4) above, further comprising a compound capable of decreasing the intraocular pressure.

(6) The agent for ameliorating ocular circulatory disorder of any of (1) to (5) above, which is in the form of an eye drop.

(7) The agent for ameliorating ocular circulatory disorder of any of (1) to (5) above, which is in the form of an eye ointment.

(8) The agent for ameliorating ocular circulatory disorder of any of (1) to (7) above, which is an agent for the prophylaxis and treatment of a disease caused by a circulatory disorder in the ciliary artery system.

(9) The agent for ameliorating ocular circulatory disorder of (8) above, wherein the disease caused by the circulatory disorder in the ciliary artery system is a disease selected from the group consisting of normal tension glaucoma, retinitis pigmentosa, macular degeneration, ischemic optic neuropathy and iridocyclitis.

(10) The agent for ameliorating ocular circulatory disorder of any of (1) to (7) above, which is an agent for the prophylaxis and treatment of a disease caused by a circulatory disorder of the central retinal artery system.

(11) The agent for ameliorating ocular circulatory disorder of (10) above, wherein the disease caused by the circulatory disorder in the central retinal artery system is a disease selected from the group consisting of retina artery occlusion, retinal vein occlusion, diabetic retinopathy, ischemic optic neuropathy, choroidal disease following retinal lesion and retinochoroidal disease accompanied by systemic disease.

(12) A method for ameliorating an ocular circulatory disease, comprising administering a compound the formula (I)

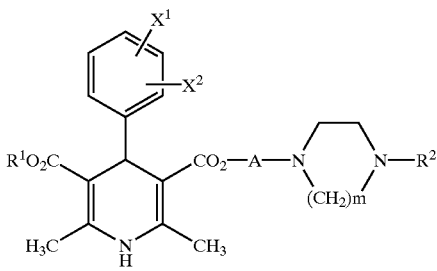

wherein
$X^1$ and $X^2$ are the same or different and each is hydrogen atom, fluoromethyl, fluoromethoxy, halogen, cyano or nitro;
$R^1$ is lower alkyl;
$R^2$ is acyl, alkoxycarbonyl, acylalkyl N-alkyl-substituted carbamoylalkyl, alkoxyalkyl, alkoxycarbonylalkyl, acyloxyalkyl, nitratoalkyl, cyanoalkyl, heterocyclic alkyl haloalkyl, alkenyl or alkynyl;
A is alkylene having a carbon atom bonded with two alkyl and having a total number of carbon atoms of 5 or more; and
m is an integer of 1 to 3,
or an acid addition salt, in an amount effective for ameliorating the ocular circulation disorder.

(13) The method for ameliorating the ocular circulation disorder of (12) above, wherein, in the formula (I), $R^2$ is acylalkyl, N-alkyl-substituted carbamoylalkyl, alkoxyalkyl, cyanoalkyl, heterocyclic alkyl, haloalkyl, alkenyl or alkynyl

(14) The method for ameliorating the ocular circulation disorder of (12) above, wherein, in the formula (I), $R^2$ is alkenyl or alkynyl.

(15) The method for ameliorating the ocular circulation disorder of (12) above, wherein, in the formula (I), A is alkylene having a carbon atom bonded with two alkyl and having a total number of carbon atoms of 5 to 10.

(16) The method for ameliorating the ocular circulation disorder of any of (12) to (15) above, wherein the compound capable of deceasing the intraocular pressure is concurrently administered.

(17) The method for ameliorating the ocular circulation disorder of any of (12) to (16) above, wherein the 1,4-dihydropyridine derivative or an acid addition salt is administered in the form of an eye drop.

(18) The method for ameliorating the ocular circulation disorder of any of (12) to (16) above, wherein the 1,4-dihydropyridine derivative or an acid addition salt is administered in the form of an eye ointment.

(19) The method for ameliorating the ocular circulation disorder of any of (12) to (18) above, which is a method for the prophylaxis and treatment of a disease caused by a circulatory disorder in the ciliary artery system.

(20) The method for ameliorating the ocular circulation disorder of (19) above, wherein the disease caused by the circulatory disorder in the diary artery system is a disease selected from the group consisting of normal tension glaucoma, retinitis pigmentosa, macular degeneration, ischemic optic neuropathy and iridocyclitis.

(21) The method for ameliorating the ocular circulation disorder of any of (12) to (18) above, which is a method for the prophylaxis and treatment of a disease caused by a circulatory disorder of the central retinal artery system.

(22) The method for ameliorating the ocular circulation disorder of (21) above, wherein the disease caused by the circulatory disorder in the central retinal artery system is a disease selected from the group consisting of retinal artery occlusion, retinal vein occlusion, diabetic retinopathy, ischemic optic neuropathy, choroidal disease following retinal lesion and retinochoroidal disease accompanied by systemic disease.

(23) Use of a 1,4-dihydropyridine derivative of the formula (I)

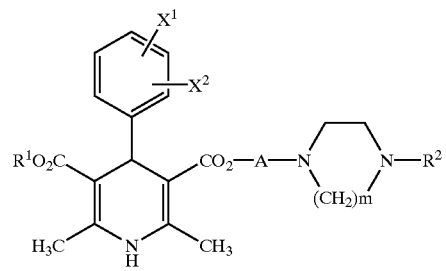

wherein
$X^1$ and $X^2$ are the same or different and each is hydrogen atom, fluoromethyl, fluoromethoxy, halogen, cyano or nitro;
$R^1$ is lower alkyl;
$R^2$ is acyl, alkoxycarbonyl, acylalkyl, N-alkyl-substituted carbamoylalkyl, alkoxyalkyl, alkoxycarbonylalkyl, acyloxyalkyl, nitratoalkyl, cyanoalkyl heterocyclic alkyl, haloalkyl, alkenyl or alkynyl;
A is alkylene having a carbon atom bonded with two alkyl and having a total number of carbon atoms of 5 or more; and
m is an integer of 1 to 3,
or an acid addition salt for the production of an agent for ameliorating an ocular circulatory disorder.

(24) The use of (23) above, wherein, in the formula (I), $R^2$ is acylalkyl, N-alkyl-substituted carbamoylalkyl, alkoxyalkyl, cyanoalkyl, heterocyclic alkyl, haloalkyl, alkenyl or alkynyl.

(25) The use of (23) above, wherein, in the formula (I), $R^2$ is alkenyl or alkynyl.

(26) The use of (23) above, wherein, in the formula (I), A is alkylene having a carbon atom bonded with two alkyl and having a total number of carbon atoms of 5 to 10.

(27) The use of any of (23) to (26) above, wherein the agent for ameliorating the ocular circulation disorder further comprises a compound capable of decreasing the intraocular pressure.

(28) The use of any of (23) to (27) above, wherein the agent for ameliorating the ocular circulation disorder is in the form of an eye drop.

(29) The use of any of (23) to (27) above, wherein the agent for ameliorating the ocular circulation disorder is in the form of an eye ointment.

(30) The use of any of (23) to (29) above, wherein the agent for ameliorating the ocular circulation disorder is an agent for the prophylaxis and treatment of a disease caused by a circulatory disorder in the ciliary artery system.

(31) The use of (30) above, wherein the disease caused by the circulatory disorder in the ciliary artery system is a disease selected from the group consisting of normal tension glaucoma, retinitis pigmentosa, macular degeneration, ischemic optic neuropathy and iridocyclitis.

(32) The use of any of (23) to (29) above, wherein the agent for ameliorating the ocular circulation disorder is an agent for the prophylaxis and treatment of a disease caused by a circulatory disorder of central retinal artery system.

(33) The use of (32) above, wherein the disease caused by the circulatory disorder in the central retinal artery system is a disease selected from the group consisting of retinal artery occlusion, retinal vein occlusion, diabetic retinopathy, ischemic optic neuropathy, choroidal disease following retinal lesion and retinochoroidal disease accompanied by systemic disease.

DETAILED DESCRIPTION OF THE INVENTION

Figure 1:
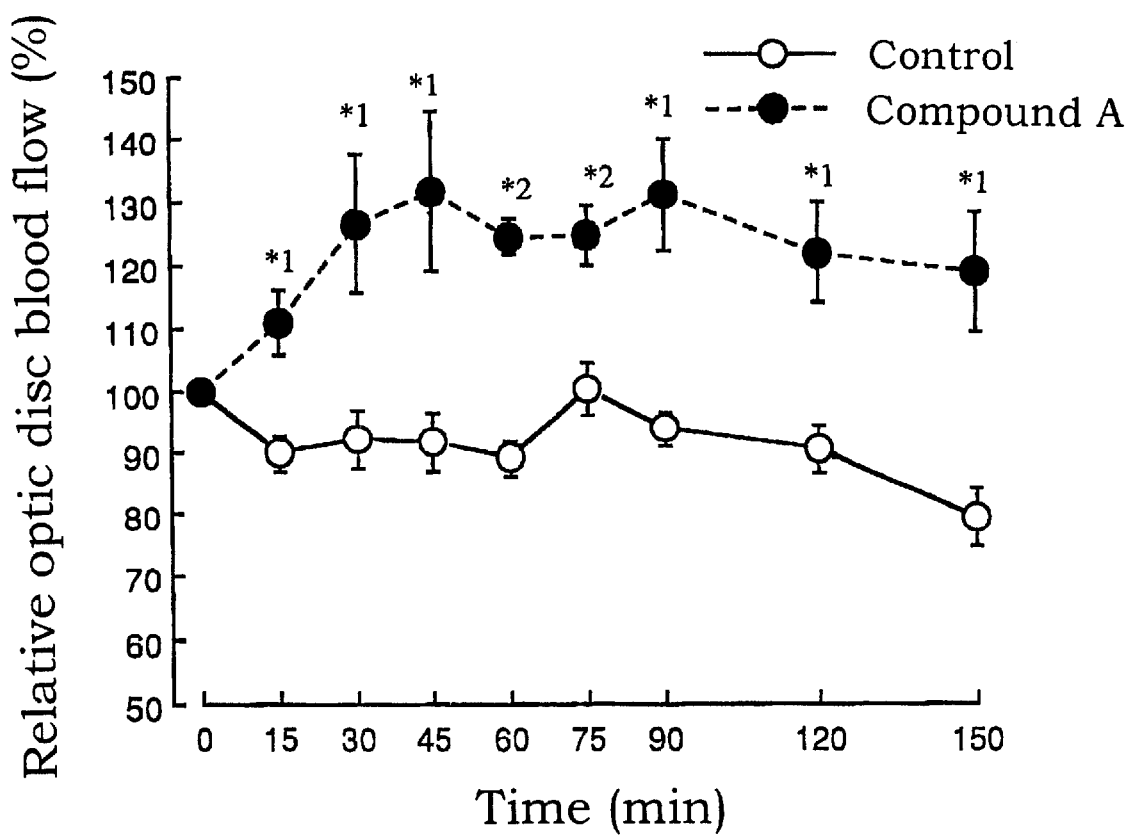
FIG. 1 is a graph showing the time course changes in relative optic disc blood flow (blood flow at each point in time when the initial value is 100%) in normal eye after instillation of a 0.1% ophthalmic solution (containing 0.1% of the compound A of the present invention) in Experimental Example 1, wherein the axis of abscissa shows time (min) and the axis of ordinate shows relative optic disc blood flow (%). Each value shows mean±standard error (n=6). Significant difference from the control is found in *1; $P<0.01$, *2; $P<0.001$ (paired t-test). The black circle shows instillation of a 0.1% ophthalmic solution and white circle shows instillation of physiological saline.

The present invention is described in detail in the following. The agent for ameliorating ocular circulatory disorder of the present invention contains the above-mentioned 1,4-dihydropyridine derivative of the formula (I) or an acid addition salt thereof as an active ingredient.

In the present specification, $C_X$ means that the number of carbon is X, for example, C1–C4 means that the number of carbon atoms is 1 to 4.

In the formula (I), fluoromethyl at $X^1$ and $X^2$ is monofluoromethyl, difluoromethyl or trifluoromethyl; fluoromethoxy at $X^1$ and $X^2$ is monofluoromethoxy, difluoromethoxy or trifluoromethoxy, and halogen at $X^1$ and $X^2$ is fluorine atom, chlorine atom, bromine atom or iodine atom.

In the formula (I), lower alkyl at $R^1$ is linear, branched or cyclic and preferably has 1 to 4 carbon atoms. Examples thereof include methyl ethyl, n-propyl, isopropyl, n-butyl, isobutyl, sec-butyl, tert-butyl, cyclopropylmethyl and the like.

In the formula (I), acyl at $R^2$ may be aliphatic acyl, aromatic acyl or heterocyclic acyl. The aliphatic acyl may be saturated or unsaturated, linear or branched, and preferably has 1 to 5 carbon atoms. When it is unsaturated, it preferably has one or two double bonds or triple bonds. An aromatic acyl or heterocyclic acyl has a structure wherein carbonyl is directly bonded to aromatic group or heterocycle; or a carbonyl group is bonded to aromatic group via aliphatic group [e.g., saturated or unsaturated C1–C3 group, having, when it is unsaturated, 1 or 2 double bond(s) or triple bond(s)]. The heterocycle is preferably a 5 or 6-membered ring, particularly one wherein the hetero atom is preferably nitrogen atom or oxygen atom. The aliphatic group, aromatic group and hetero group of aliphatic acyl, aromatic acyl and heterocyclic acyl may be substituted by halogen (e.g., chlorine atom, bromine atom and the like), hydroxyl group, carboxyl group, alkoxyl group, acyl group, acylamino group and the like.

Preferable examples of acyl at $R^2$ include formyl, acetyl, crotonoyl, acryloyl, propioloyl, benzoyl, phenylacetyl, cinnamoyl, p-acetoaminobensoyl, m-methoxybenzoyl, m-dimethylaminobenzoyl, p-hydroxycinnamoyl, furoyl, nicotinoyl, piperidinomethylcarbonyl and the like.

Alkoxycarbonyl at $R^2$ is alkoxycarbonyl having linear or branched C1–C5 alkoxy, and preferable examples include methoxycarbonyl, ethoxycarbonyl, propoxycarbonyl, tert-butoxycarbonyl and the like.

The acyl of acylalkyl at $R^2$ is exemplified by those mentioned above, wherein alkyl may be linear or branched C1–C5 alkyl. Preferable examples include phenacyl, acetonyl, methylcarbonylethyl, pyrrolidinocarbonylmethyl and the like.

The N-alkyl-substituted carbamoylalkyl at $R^2$ may be mono-substituted or di-substituted. The alkyl as the substituent may be linear or branched C1–C5 alkyl. Preferable examples include methylcarbamoylmethyl, piperadinocarbamoylmethyl, dimethylcarbamoylmethyl and the like.

The alkoxy and alkyl of alkoxyalkyl at $R^2$ is exemplified by linear or branched C1–C5 alkoxy and C1–C5 alkyl Preferable examples include methoxyethyl, ethoxyethyl, methoxypropyl and the like.

The alkoxy and alkyl of alkoxycarbonylalkyl at $R^2$ are exemplified by linear or branched C1–C5 alkoxy and C1–C5 alkyl. Preferable examples include methoxycarbonylmethyl, ethoxycarbonylmethyl, ethoxycarbonylethyl and the like.

The acyl of acyloxyalkyl at $R^2$ is exemplified by those mentioned above, wherein alkyl may be linear or branched C1–C5 alkyl. Preferable examples include acetoxyethyl benzoyloxyethyl and the like.

The alkyl of nitratoalkyl at $R^2$ may be, for example, linear or branched C1–C5 alkyl. Preferable examples include nitratoethyl, nitratopropyl and the like.

The alkyl of cyanoalkyl at $R^2$ may be linear or branched C1–C5 alkyl Preferable examples include cyanomethyl, cyanoethyl and the like.

The heterocyle of heterocyclic alkyl at $R^2$ is preferably 5- or 6-membered ring, particularly preferably one wherein hetero atom is nitrogen atom or oxygen atom. Examples thereof include piperidino, morpholino and the like. The alkyl may be, for example, linear or branched C1–C5 alkyl Preferable examples include piperidinoethyl, morpholinoethyl and the like.

The halogen of haloalkyl at $R^2$ is exemplified by fluorine atom, chlorine atom, bromine atom and the like and alkyl is exemplified by linear or branched C1–C5 alkyl. Preferable examples include trihalogen-substituted methyl (e.g., trifluoromethyl), monohalogen-substituted ethyl (e.g., monofluoroethyl) and the like.

The alkenyl and alkynyl at $R^2$ are exemplified by linear or branched C2–C5 alkenyl and C2–C5 alkynyl, such as vinyl, propenyl, isopropenyl, butenyl, ethynyl, propynyl, butynyl, pentynyl and the like.

In the formula (I), alkylene having a carbon atom bonded with two all and having a total number of atoms of 5 or more represented by A may be linear or branched and preferably has 10 or less, particularly 8 or less carbon atoms. Examples thereof include 2,2-dimethyltetramethylene, 2,2-dimethylpentamethylene, 2,2dimethylhexamethylene, 2,2-dimethyltrimethylene, 1,1-dimethyltrimethylene and the like, with preference given to 2,2-dimethyltrimethylene.

The m is preferably 1 or 2.

The acid addition salt of the compound (I) of the present invention is free of particular limitation as long as it is pharmacologically acceptable and nontoxic, and is exemplified by inorganic acid salt (e.g., hydrochloride, hydrobromide, phosphate, sulfate), organic acid salt (e.g., acetate, succinate, maleate, fumarate, malate, tartrate, methanesulfonate) and the like.

The 1,4-dihydropyridine derivative of the formula (I) wherein $R^2$ is acylalkyl, N-alkyl-substituted carbamoyalkyl alkoxyalkyl, cyanoalkyl, heterocyclic alkyl, haloalkyl, alkenyl or alkynyl (particularly, $R^2$ is alkenyl or alkynyl) and an acid addition salt thereof are superior in these actions and show particularly superior dissolution in water.

The 1,4-dihydropyridine derivative (I) of the present invention is exemplified by the following compounds.

3-(4-allyl-1-piperazinyl)-2,2-dimethylpropyl methyl 2,6-dimethyl-4-(m-nitrophenyl)-1,4-dihydropyridine-3,5-dicarboxylate dihydrochloride (hereinafter to be referred to as compound A of the present invention)

3-[4-(2-propenyl)-1-piperazinyl]-2,2-dimethylpropyl methyl 2,6-dimethyl-4-(m-nitrophenyl)-1,4-dihydropyridine-3,5-dicarboxylate dihydrochloride 3-(4-cyanomethyl-1-piperazinyl)-2,2-dimethylpropyl methyl 2,6-dimethyl-4-(m-nitrophenyl)-1,4dihydropyridine-3,5-dicarboxylate dihydrochloride 3-[4-(2-methyl-2-propenyl)-1-homopiperazinyl]-2,2-dimethylpropyl methyl 2,6-dimethyl-4-(m-nitrophenyl)-1,4-dihydropyridine-3,5-dicarboxylate dihydrochloride 3-(4-alkyl-1-homopiperazinyl)-2,2-dimethylpropyl methyl 2,6-dimethyl-4-(m-nitrophenyl)-1,4-dihydropyridine-3,5-dicarboxylate dihydrochloride 3-[4-(tert-butyloxycarbonyl)-1-homopiperazinyl]-2,2-dimethylpropyl methyl 2,6-dimethyl-4-(m-nitrophenyl)-1,4-dihydropyridine-3,5-dicarboxylate 3-(4-formyl-1-homopiperazinyl)-2,2-dimethylpropyl methyl 2,6-dimethyl-4-(m-nitrophenyl)-1,4-dihydropyridine-3,5-dicarboxylate.

The 1,4-dihydropyridine derivative (I) of the present invention has a blood flow increasing action in retinochoroid, and inhibits vasocontraction and decrease in blood flow caused by ET-1, which is one of the biological vasocontracting substances, in mammals (e.g., human, cow, horse, mouse, rat, dog, cat, rabbit and the like), and also inhibits increase in intraocular pressure when in the form of an eye drop.

The 1,4-dihydropyridine derivative (I) of the present invention is a calcium antagonist, but nicardipine, which is also a calcium antagonist, does not show such effect. The effect is characteristic of the compound of the present invention.

Accordingly, 1,4-dihydropyridine derivative (I) and an acid addition salt thereof are useful as an agent for ameliorating ocular circulatory disorder in mammals such as human, cow, horse, dog, mouse, rat and the like, and they are expected to be applicable for the prophylaxis and treatment of the diseases such as, from among the types of glaucoma, particularly normal tension glaucoma caused by ocular circulation disorder, retinitis pigmentosa, macular degeneration, ischemic optic neuropathy, iridocyclitis, retinal artery occlusion, retinal vein occlusion, diabetic retinopathy, choroidal disease following retinal lesion, retinochoroidal disease accompanied by systemic disease and the like.

The agent for ameliorating ocular circulatory disorder of the present invention may contain a compound capable of decreasing intraocular pressure, in addition to the 1,4-dihydropyridine derivative (I). The compound capable of decreasing intraocular pressure to be used in the present invention is free of any particular limitation and may be a known compound. Examples thereof include moieties (e.g., pilocarpine, carbachol, acetylcholine esterase inhibitor), sympathetic agent (e.g., epinephrine, dipivalyl epinephrine, paraaminoclonidine, α-methyldipivalyl epinephrine, apraclonidine, clonidine), β-blocker (e.g., betaxolol, levobunolol, timolol), carbonate dehydratase inhibitor (e.g., acetazolamide, methazolamide, ethoxzolamide, MK507) and the like. Of these, preferred are timolol, betaxolol, levobunolol, carteolol pilocarpine, carbachol, MK927, MK507, AL04414, AL04623, AL04862, epinephrine, dipivalyl epinephrine, α-methyldipivalylepinephrine, apraclonidine and clonidine.

The concurrent use of a compound capable of decreasing intraocular pressure makes possible the prophylaxis and treatment of glaucoma as a whole by the agent for ameliorating ocular circulatory disorder of the present invention, since the agent is also effective against glaucoma caused by high intraocular pressure, in addition to glaucoma caused by circulatory disorder (e.g., normal tension glaucoma).

When the 1,4-dihydropyridine derivative (I) and an acid addition salt thereof are used as pharmaceutical products, they can be administered orally or parenterally. The administration route includes oral administration in tablet, capsule, syrup and the like, and parenteral administration of liquid injection of solution, emulsion, suspension and the like, parenteral administration of external preparation such as ointment particularly eye ointment), cream, suppository, poultice, eye drop, nasal drop, inhalent, liniment, aerosol and the like. In consideration of influence on other circulatory system, the particularly preferable dosage form is an eye drop.

The 1,4-dihydropyridine derivative (I) and an acid addition salt thereof have high solubility in water as compared to conventional calcium antagonists such as nicardipine and the like. They can be easily prepared into an eye drop and the like, which is clinically extremely easy to handle.

When an eye drop is prepared, the pH thereof is generally set to about 3 to 7, preferably 4 to 6.

The preparation in the above-mentioned dosage form can be produced by admixing additives typically necessary for usual preparation, and processing according to a conventional method. For example, the additives to be used for an eye drop include the following.

Buffering agent may be phosphate buffer, berate buffer, citrate buffer, tartrate buffer, acetate buffer, amino acid and the like. Preferred are buffers having buffer capability in the pH range of from 2 to 9.

Examples of isotonizing agent include saccharides such as sorbitol, glucose, mannitol and the like, polyhydric alcohol such as glycerol, polyethylene glycol, propylene glycol and the like, and salt such as sodium chloride and the like.

Examples of preservative include benzalkonium chloride, benzetonium chloride, p-hydroxybenzoic acid esters such as methyl p-hydroxybenzoate, ethyl p-hydroxybenzoate and the like, benzyl alcohol, phenetyl alcohol, sorbic acid and a salt thereof, timerosal, chlorobutanol and the like.

Examples of thickener include hydroxyethyl cellulose, hydroxypropyl cellulose, methyl cellulose, hydroxypropylmethyl cellulose, carboxymethyl cellulose and a salt thereof.

Examples of solubilizer (stabilizer) include water soluble polymer such as cyclodextrin, polyvinylpyrrolidone and the like, surfactant such as polysorbate 80 and the like.

Examples of chelating agent include sodium edetate, sodium citrate, condensed sodium phosphate and the like.

Examples of suspending agent include surfactant such as polysorbate 80 and the like, and water soluble polymer such as sodium methyl cellulose, hydroxypropyl methyl cellulose, methyl cellulose and the like.

While the dose and administration frequency vary depending on symptom, age, body weight and administration route, when, for example, administered as an eye drop to an adult, a preparation containing 1,4-dihydropyridine derivative (I) and a compound that decreases intraocular pressure each in a concentration of 0.0001–10 w/v %, preferably 0.001–5 w/v %, can be administered several times a day, preferably 1 to 6 times, several drops a time, preferably 1 to 3 drops. When in use as an eye ointment, a preparation containing 1,4-dihydropyridine derivative (I) and a compound that decreases intraocular pressure each in a concentration of 0.0001–10 w/v %, preferably 0.001–5 w/v %, can be applied several times a day, preferably 1 to 6 times.

EXAMPLES

The present invention is explained in more detail in the following by way of Examples and Experimental Examples.

Example 1

An ophthalmic solution having the following composition, that contained the compound of the present invention, was prepared.

| | |
|---|---|
| Compound of the present invention | 0.1 g |
| Sodium acetate | 0.1 g |
| Sodium chloride | 0.9 g |
| Benzalkonium chloride | 0.005 g |
| Acetic acid | suitable amount |
| Sterile purified water | suitable amount |
| Total amount | 100 ml (pH 5) |

Example 2

An ophthalmic solution having the following composition, that contained the compound of the present invention, was prepared.

| | |
|---|---|
| Compound of the present invention | 0.01 g |
| Sodium acetate | 0.1 g |
| β-cyclodextrin | 0.190 g |
| Sodium chloride | 0.9 g |
| Benzalkonium chloride | 0.005 g |
| Acetic acid | suitable amount |
| Sterile purified water | suitable amount |
| Total amount | 100 ml (pH 5) |

Example 3

An ophthalmic solution having the following composition, that contained the compound of the present invention, was prepared.

| | |
|---|---|
| Compound of the present invention | 0.001 g |
| Sodium acetate | 0.1 g |
| Sodium edetate | 0.01 g |
| Sodium chloride | 0.9 g |
| Benzalkonium chloride | 0.005 g |
| Acetic acid | suitable amount |
| Sterile purified water | suitable amount |
| Total amount | 100 ml (pH 5) |

Example 4

An ophthalmic solution having the following composition, that contained the compound of the present invention, was prepared.

| | |
|---|---|
| Compound of the present invention | 0.1 g |
| Sodium acetate | 0.1 g |
| Sodium edetate | 0.005 g |
| Sodium chloride | 0.9 g |
| Benzalkonium chloride | 0.005 g |
| Acetic acid | suitable amount |
| Sterile purified water | suitable amount |
| Total amount | 100 ml (pH 5) |

Example 5

An ophthalmic solution having the following composition, that contained the compound of the present invention, was prepared.

| | |
|---|---|
| Compound of the present invention | 0.1 g |
| Timolol | 0.5 g |
| Sodium acetate | 0.1 g |
| Sodium edetate | 0.005 g |
| Sodium chloride | 0.9 g |
| Benzalkonium chloride | 0.005 g |
| Acetic acid | suitable amount |
| Sterile purified water | suitable amount |
| Total amount | 100 ml (pH 5) |

Example 6

An eye ointment containing the compound of the present invention was prepared.

| | |
|---|---|
| Compound of the present invention | 0.1 g |
| Liquid paraffin | 10 g |
| Sterile purified water | suitable amount |
| Total amount | 100 g |

Experimental Materials
<Animals Used>

Male Dutch color house rabbits weighing about 2 kg were purchased from Fukusaki Rabbitery Co-operation and used upon confirmation of the absence of abnormality in the eye. The rabbits were bred at temperature 23±3° C. and humidity 55±10% on solid feed (Labo R Stock manufactured by NIHON NOSAN KOGYO K.K, 100 g a day), while allowing free access to tap water.

<Test Drugs>

The ophthalmic solution prepared in Example 1 contaning the compound A of the present invention in a concentration of 0.1% (hereinafter to be sometimes referred to as 0.1% ophthalmic solution) was used. As a control drug, 0.1% nicardipine hydrochloride solution (trademark: Perdipine injection 2 mg, manufactured by YAMANOUCHI PHARMACEUTICAL CO., LTD., hereinafter to be sometimes referred to as nicardipine hydrochloride-containing preparation).

Experimental Example 1

Effects on Blood Flow of Normal Eye

A) Measurement of Blood Flow in Optic Disc (1) Puncture of Different Electrode

The rabbits were placed in a retaining cage and optic disc was examined for abnormality upon mydriasis with mydrin P (trademark, manufactured by SANTEN PHARMACEUTICAL CO., LTD.) Urethane (dissolved in distilled water in 20%, 1 g/kg) was subcutaneously administered in the abdomen for systemic anesthesia One or two hours later, a plate type indifferent electrode (manufactured by Biomedical Science, BE-R10) was subcutaneously attached to the head under stable anesthesia The upper and lower eyelids of both eyes were pulled open upward and downward with a suture and conjunctiva at 6 o'clock was incised. The suture was passed through subrectus muscle and pulled downward to fix the eyeball. Sclera at about 3 mm from corneal limbus at 6 o'clock was opened with a 27 G needle and a needle different electrode (manufactured by Biomedical Science, BE-NSP 450-30) was punctured from there through vitreous body into optic disc. The opening of the sclera and different electrode were fixed with Aron Alpha (trademark, manufactured by KONISHI CO., LTD.)

(2) Measurement of Blood Flow

After puncture of different electrode, the rabbits were stood for about one hour. The rabbits were set to inhale 10% hydrogen for about 5 min, and the height from the base line to the curve of the clearance curve depicted on a recorder was measured at 12-second intervals staring from the peak The relationship between the value obtained and the time was plotted on a semilogarithm graph. A straight line was drawn to gather a greatest number possible of measurement dots and half-life (T½) was calculated from the straight line. The blood flow was determined from the following theoretical formula of Kety (Journal of Clinical Investigate, vol. 27, pp. 476–483 (1948)). The test was started after measurement of blood flow at 15-minute intervals and after the measurement of stable values became available. The initial value was an average of two measurements before starting the test.

$$\text{Blood flow (ml/min/ 100 g)} = 69.3/T\!\tfrac{1}{2}$$

2) Instillation Method

A 0.1% ophthalmic solution or a nicardipine hydrochloride-containing preparation (20 μl) was instilled into one eye and physiological saline (20 μl) was instilled into the other eye.

3) Results

Figure 2:
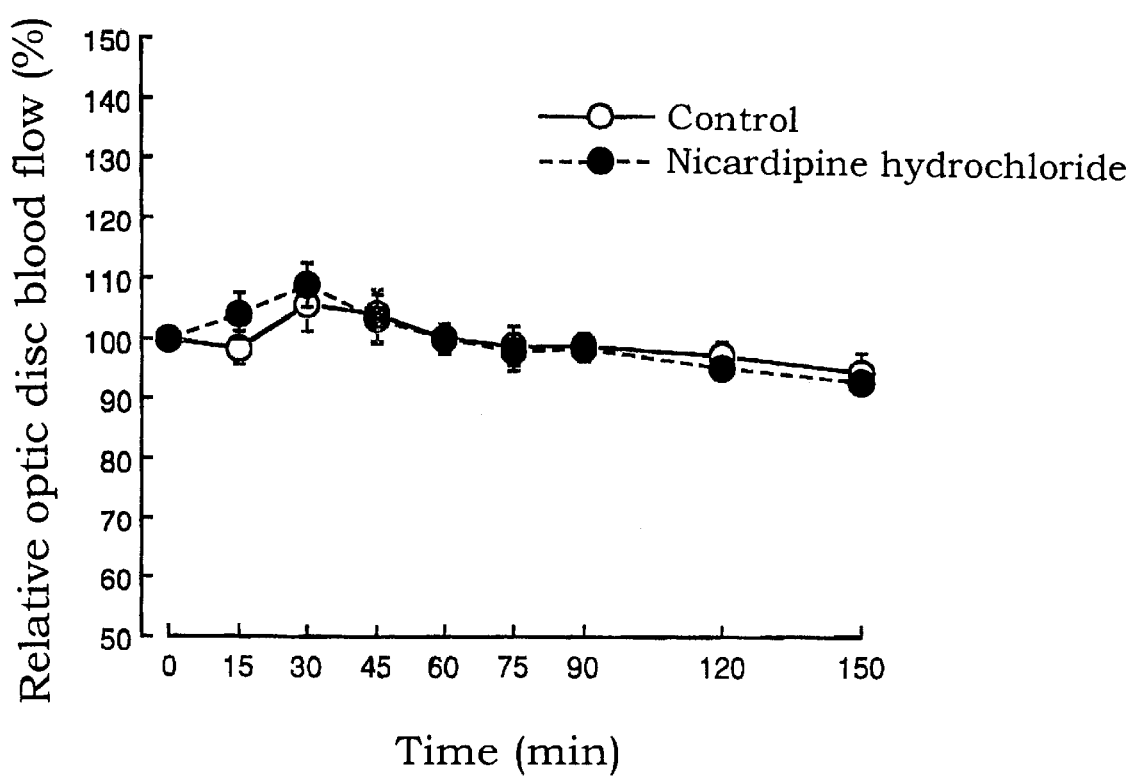
FIG. 2 is a graph showing the time course changes in relative optic disc blood flow in normal eye after instillation of a preparation containing nicardipine hydrochloride in Experimental Example 1, wherein the axis of abscissa shows time (min) and the axis of ordinate shows relative optic disc blood flow (%). Each value shows mean±standard error (n=6). The black circle shows instillation of a preparation containing nicardipine hydrochloride and the white circle shows instillation of physiological saline.

The relative optic disc blood flow (blood flow when initial value was 100%) in the normal eye after instillation of the 0.1% ophthalmic solution and nicardipine hydrochloride-containing preparation is shown in FIG. 1 and FIG. 2, respectively. The initial value of the blood flow before instillation was 27.4–58.5 ml/min/ 100 g.

The eye after instillation of the 0.1% ophthalmic solution showed a significantly increased blood flow after 15 min as compared to the eye after instillation of physiological saline, and at 45 min after installation, the maximum increase of 31.7% was obtained as compared to the initial value. The action lasted for 180 min after the instillation. On the other hand, the eye after instillation of the nicardipine hydrochloride-containing preparation showed a 5–10% increase in blood flow as compared to the initial value, for 30 min after instillation, but the eye instilled with physiological saline also showed an increase. Thus, significant difference was not observed. At any point in time thereafter, increase in blood flow could not be found.

It is postulated that the 0.1% ophthalmic solution increased the blood flow in the optic disc because the compound of the present invention acted on vascular smooth muscle in the optic disc via cornea to cause vasodilation, and because the compound of the present invention caused dilation of long posterior ciliary artery via sclera to ultimately increase the retinal circulation.

Experimental Example 2

Effects on ET-1 Ocular Circulation Disorder

A) Measurement of Optic Disc Blood Flow

Measured in the same manner as in Experimental Example 1.

2) Instillation Method

Instilled in the same manner as in Experimental Example 1.

3) Administration of ET-1

At 60 minutes after the instillation of the drug, $10^{-6}$M ET-1 (10 μl, derived from human, manufactured by SIGMA) was injected into the central part of the vitreous body of both eyes while observing the eye ground with a vitrectomy lens.

4) Observation of Retinal Blood Vessel Diameter

The retinal blood vessel diameter was microscopically observed before injection of ET-1 and after injection at 30-minute intervals for 150 minutes using an inverted image mirror after measurement of blood flow according to the following evaluation criteria.

| | |
|---|---|
| Normal retinal blood vessel diameter | 0 |
| Decreased to ¾ of retinal blood vessel diameter | 1 |
| Decreased to ½ of retinal blood vessel diameter | 2 |
| Decreased to ¼ of retinal blood vessel diameter | 3 |
| Presence of blood vessel barely confirmed or Complete occlusion | 4 |

5) Results

Figure 3:
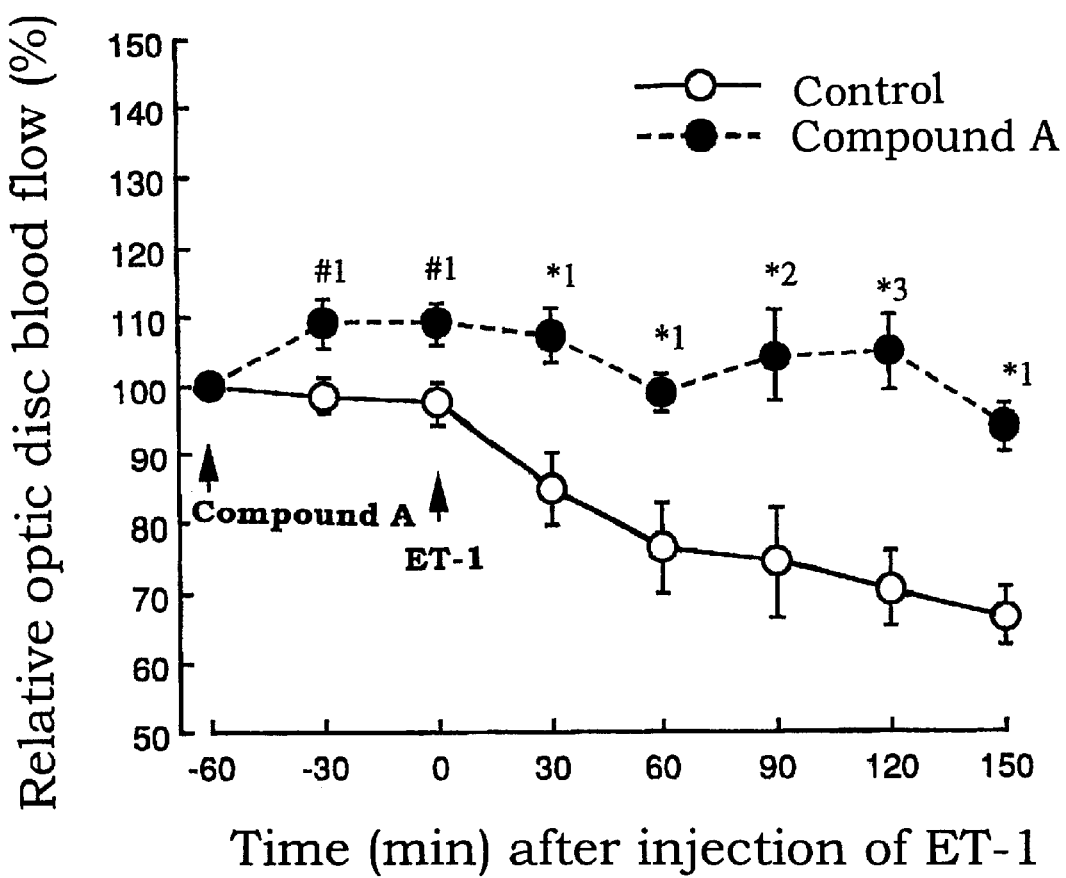
FIG. 3 is a graph showing the time course changes in relative optic disc blood flow upon injection of ET-1 after instillation of a 0.1% ophthalmic solution (containing 0.1% of the compound A of the present invention) in Experimental Example 2, wherein the axis of abscissa shows time (min) when the injection of ET-1 is 0 and the axis of ordinate shows relative optic disc blood flow (%). Each value shows mean±standard error (n=7). A significant difference from control is found in #1; $P<0.05$. A significant difference from control is found in *1; $P<0.05$,*2; $P<0.01$,*3; $P<0.001$ (paired t-test) in the amount of difference at each point in time from that immediately before the addition of ET-1. The black circle shows instillation of a 0.1% ophthalmic solution and white circle shows instillation of physiological saline.
Figure 4:
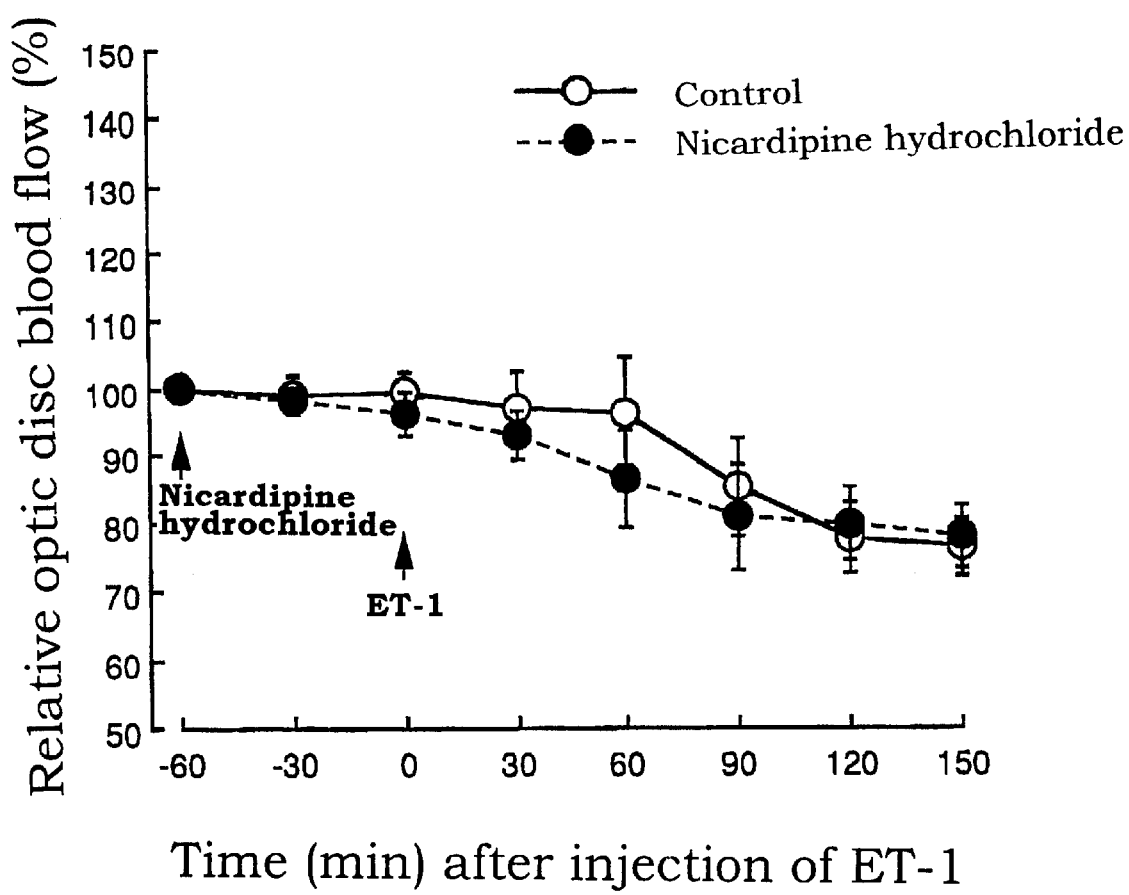
FIG. 4 is a graph showing the time course changes in relative optic disc blood flow upon injection of ET-1 after instillation of a preparation containing nicardipine hydrochloride in Experimental Example 2, wherein the axis of abscissa shows time (min) when the injection of ET-1 is 0 and the axis of ordinate shows relative optic disc blood flow (%). Each value shows mean±standard error (n=6). The black circle shows instillation of a preparation containing nicardipine hydrochloride and white circle shows instillation of physiological saline.

The effect on the decrease in relative optic disc blood flow due to ET-1 injection, after instillation of 0.1% ophthalmic solution and nicardipine hydrochloride-containing preparation is shown in FIG. 3 and FIG. 4, respectively. The initial value of blood flow before instillation was 32.3–67.1 ml/min/ 100 g.

The eye after instillation of the 0.1% ophthalmic solution showed a significant 9% increase in blood flow after 30 min from the instillation as compared to the initial value. The action lasted for 60 minutes after the instillation. ET-1 was injected at this point. As a result, the eye after instillation of physiological saline showed a 12% decrease in blood flow 30 min after instillation as compared to immediately before the ET-1 injection, and the 32% maximum decrease after 150 min.

In contrast, the eye instilled with the 0.1% ophthalmic solution showed the same initial value of blood flow at any point in time after injection of ET-1. The 0.1% ophthalmic solution therefore completely inhibited the decrease in blood flow. The eye instilled with a nicardipine hydrochloride-containing preparation showed a 10% decrease at 60 min after the injection of ET-1 as compared to that before the injection and showed the maximum 16% decrease in the blood flow at 150 minutes after the injection. As a result, the same-decrease in blood flow as achieved by the instillation of physiological saline was seen at any point in time.

Figure 5:
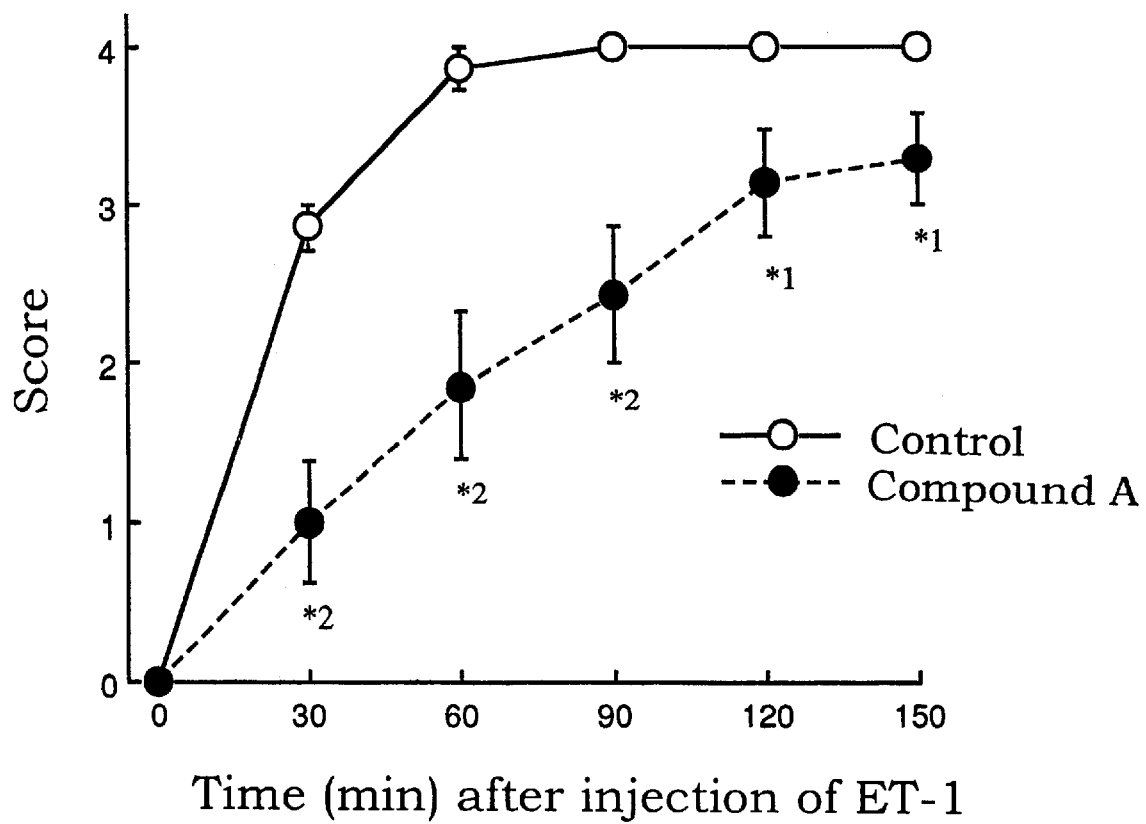
FIG. 5 is a graph showing the time course changes in vasocontraction upon injection of ET-1 after instillation of a 0.1% ophthalmic solution (containing 0.1% of the compound A of the present invention) in Experimental Example 2, wherein the axis of abscissa shows time (min) when the injection of ET-1 is 0 and the axis of ordinate shows score. Each value shows mean±standard error (n=7). A significant difference from control is found in *1; $P<0.05$,*2; $P<0.01$ paired t-test). The black circle shows instillation of a 0.1% ophthalmic solution and white circle shows instillation of physiological saline.
Figure 6:
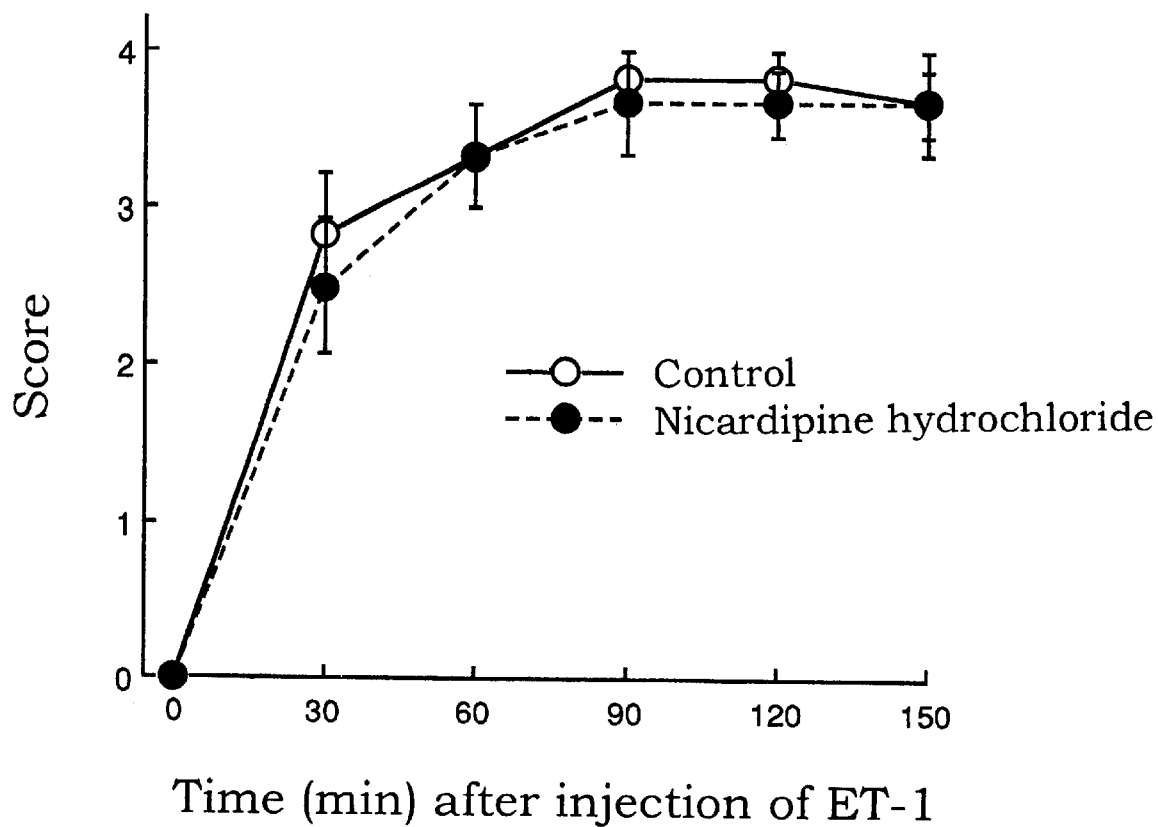
FIG. 6 is a graph showing the time course changes in vasocontraction upon injection of ET-1 after instillation of a preparation containing nicardipine hydrochloride wherein the axis of abscissa shows time (min) when the injection of ET-1 is 0 and the axis of ordinate shows score. Each value shows mean±standard error (n=6). The black circle shows instillation of nicardipine hydrochloride and white circle shows instillation of physiological saline.

The effect on the retinal vasocontraction due to ET-1 injection, after instillation of 0.1% ophthalmic solution and nicardipine hydrochloride-containing preparation, is shown in FIG. 5 and FIG. 6, respectively.

At 30 minutes after the ET-1 injection, the retinal blood vessel of the eye instilled with physiological saline contracted to ½ of the normal size, and 120 minutes later, the blood vessel almost completely occluded and the action lasted for 150 minutes after the instillation. In the eye instilled with 0.1% ophthalmic solution, the retinal vasocontraction was inhibited by 65% at 30 minutes after the ET-1 injection and the significant inhibition lasted for 150 minutes after the instillation.

In contrast, the eye instilled with nicardipine hydrochloride-containing preparation showed contraction of retinal blood vessel to ½ or less of the normal size, after 30 minutes from the ET-1 injection and complete occlusion 90 minutes later. Thus, there was found no significant difference from the eye instilled with physiological saline.

Experimental Example 3

Effects on Normal Intraocular Pressure

1) Animals Used

Male Dutch color house rabbits weighing about 2 kg were purchased from Fukusaki Rabbitery Cooperation and diurnal variation of intraocular pressure was measured in advance using a pneumatonograph (PIG), based on which 26 rabbits with stable intraocular pressure were used. The rabbits were bred at temperature 23±3° C. and humidity 55±10% on solid feed (Labo R Stock, manufactured by NIHON NOSAN KOGYO K.K., 100 g a day), while allowing free access to tap water.

2) Test Drugs

The 0.1% ophthalmic solution, and the ophthalmic solutions having a concentration of 0.0001%, 0.001% and 0.01%, which contained the compound A of the present invention (hereinafter to be respectively referred to as 0.0001% ophthalmic solution, 0.001% ophthalmic solution and 0.01% ophthalmic solution, these ophthalmic solutions optionally being generally referred to as inventive compound A-containing preparation), prepared in the same manner as in Example 1, except that the content of the compound A of the present invention was changed to 0.0001%, 0.001% and 0.01% concentration, were used. As a control drug, a 0.5% timolol maleate ophthalmic solution, which is a β-blocker, (trademark: Timoptol 0.5%, manufactured by Banyu Pharmaceutical Co., Ltd., hereinafter to be referred to as timolol ophthalmic solution) was used.

3) Test Method

A test preparation (50 μl) was instilled into one eye and physiological saline (50 μl) was instilled into the other eye of the above-mentioned male Dutch color house rabbits. Using the value immediately before instillation as the initial value, the intraocular pressure of both eyes was measured using PTG at 30 minutes, 1 hour, 2 hours and 4 hours after the instillation.

4) Results

Figure 7:
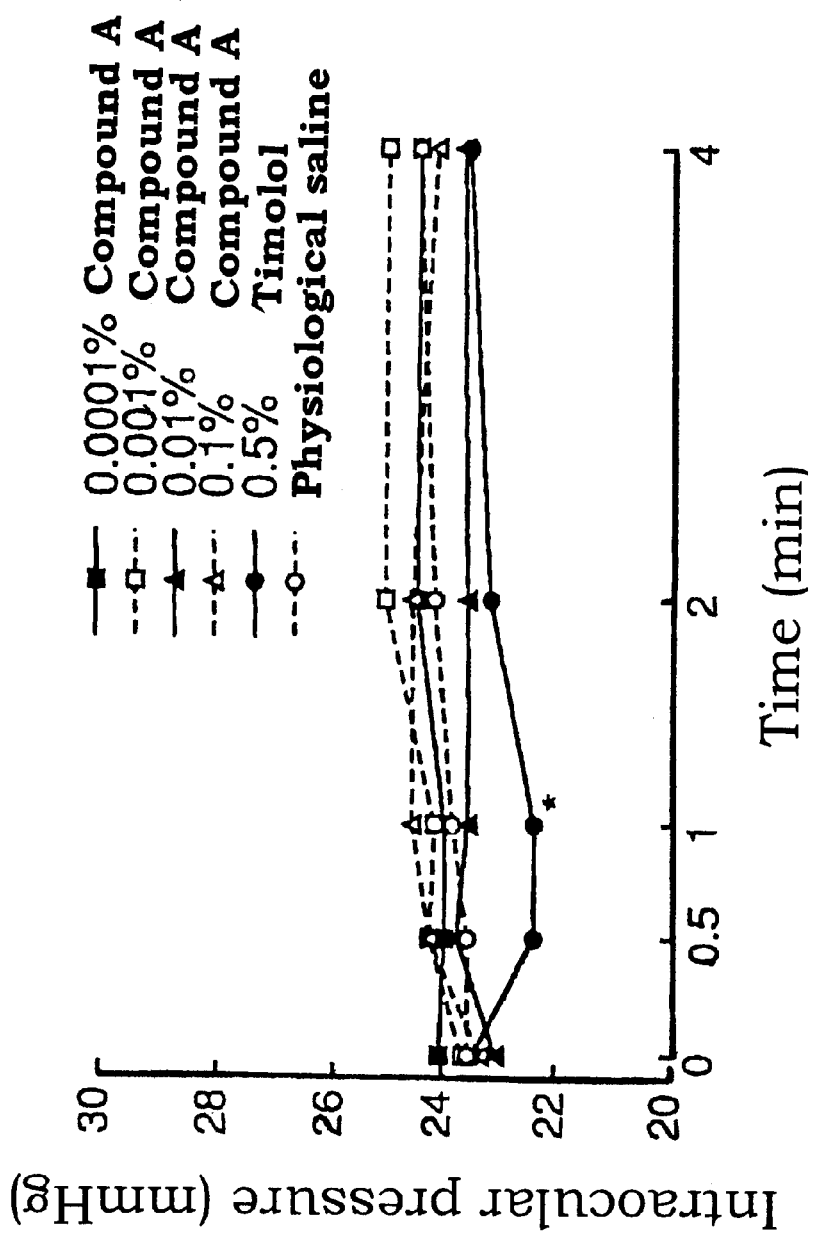
FIG. 7 is a graph showing the time course changes in intraocular pressure after instillation of a preparation containing compound A of the present invention (0.1% ophthalmic solution, 0.01% ophthalmic solution, 0.001% ophthalmic solution and 0.0001% ophthalmic solution) or a timolol ophthalmic solution. The axis of abscissa shows time (min) and the axis of ordinate shows intraocular pressure (mmHg). The black circle shows instillation of the timolol ophthalmic solution, white triangle shows that of 0.1% ophthalmic solution, black triangle shows instillation of 0.01% ophthalmic solution, white square shows instillation of a 0.001% ophthalmic solution, black square shows instillation of a 0.0001% ophthalmic solution and white circle shows instillation of physiological saline.

The time course changes in the intraocular pressure after instillation of the 0.1% ophthalmic solution and timolol ophthalmic solution are shown in FIG. 7. The inventive compound A-containing preparation of 0.1% ophthalmic solution, 0.01% ophthalmic solution, 0.001% ophthalmic solution and 0.0001% ophthalmic solution showed an intraocular pressure only within the range of physiological variation and increase was not observed. In contrast, instillation of a timolol ophthalmic solution led to a significant decrease in intraocular pressure, wherein the maximum decrease in intraocular pressure of 1.1 mmHg was seen at 30 minutes and one hour after the instillation. cl Experimental Example 4

Concurrent Use With Compound Capable of Decreasing Intraocular Pressure

1) Animals Used

Male Dutch color house rabbits weighing about 2 kg were purchased from Fukusaki Rabbitery Cooperation and habituated in a retaining cage. The diurnal variation of intraocular pressure was measured in advance using a pneumatonograph (PTG), based on which 16 rabbits with stable intraocular pressure were used. The rabbits were bred at temperature 23±3° C. and humidity 55±10% on solid feed (Labo R Stock, manufactured by NIHON NOSAN KOGYO K.K., 100 g a day), while allowing free access to tap water.

2) Test Method

A 1.0% timolol ophthalmic solution (20 μl) was instilled into both eyes of 8 house rabbits with stable intraocular pressure. At 15 minutes after the instillation, a 0.1% ophthalmic solution was instilled by 20 μl to one eye and physiological saline was instilled by 20 μl to the other eye. The intraocular pressure was measured using PTG at 30 minutes before timolol instillation, immediately before installation, 15 minutes after instillation (inmediately before instillation of 0.1% ophthalmic solution or physiological saline), and 30 minutes, 1 hour, 2 hours and 4 hours after instillation.

3) Results

Figure 8:
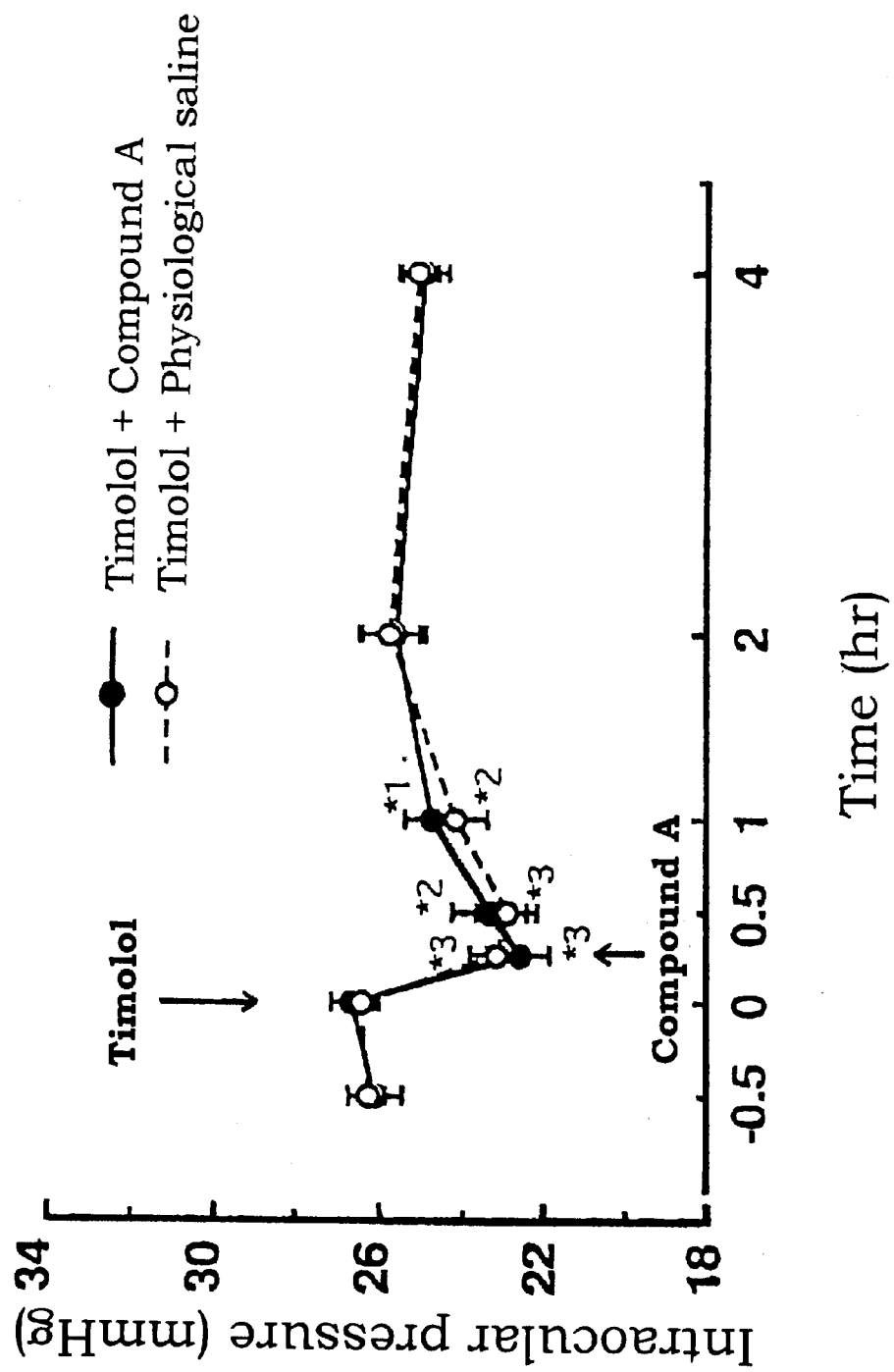
FIG. 8 is a graph showing the time course changes in intraocular pressure after instillation of a 0.1% ophthalmic solution (containing compound A of the present invention) or physiological saline after instillation of a 1.0% timolol ophthalmic solution in Experimental Example 4. The axis of abscissa shows time (hr) when the instillation of the 1.0% timolol ophthalmic solution is 0 and the axis of ordinate shows intraocular pressure (mmHg). Each value shows mean±standard error (n=8). A significant difference from the initial value is found in *1; $P<0.05$,*2; $P<0.01$,*3; $P<0.001$ (paired t-test). The black circle shows instillation of a 0.1% ophthalmic solution and white circle shows instillation of physiological saline.

The effects of timolol on the decrease in intraocular pressure by the instillation of the 0.1% ophthalmic solution after instillation of 1.0% timolol ophthalmic solution are shown in FIG. 8. At 15 minutes after timolol instillation, a decrease in intraocular pressure of 4.0 mmHg and 3.2 mmHg as compared to immediately before timolol instillation was seen in the both eyes. Inmediately thereafter, the 0.1% ophthalmic solution was instilled into one eye and physiological saline was instilled into the other eye. At 15 minutes later (30 minutes after timolol instillation), the eye instilled with 0.1% solution showed a decrease in intraocular pressure of 3.3 mmHg, and the eye instilled with physiological saline showed a decrease in intraocular pressure of 3.4 mmHg as compared to immediately before timolol instillation. Thus, no effects of instillation of the 0.1% ophthalmic solution was found. Thereafter, the both eyes regained intraocular pressure and returned to the initial value in 2 hours.

Experimental Example 5

Effects on Changes in VEP in ET-1 Ocular Circulation Disorder

1) Measurement of VEP

A stainless vis electrode (manufactured by UNIQUE MEDICAL CO., LTD.) for VEP measurement was attached to the head of the house rabbits under general anesthesia and after about 2 weeks of awakening period, the rabbits were subjected to the test. VEP was measured by shooting 1.2 J xenon arc light 32 times from 30 cm before the eye under mydriasis with mydrin P (trademark) instillation and averaged. The VEP was measured at 30 minutes, 15 minutes and immediate before ET-1 injection, and after injection at 15-minute intervals for 120 minutes.

2) Installation Method

A 0.1% ophthalmic solution was instilled by 20 μl to one eye and physiological saline was instilled by 20 μl to the other eye at 30 minutes before ET-1 injection.

3) Administration of ET-1

At 30 minutes after the drug instillation, $10^{-6}$M ET-1 (10 μl, derived from human, manufactured by SIGMA) was injected into the central part of the vitreous body of both eyes.

4) Results

Figure 9:
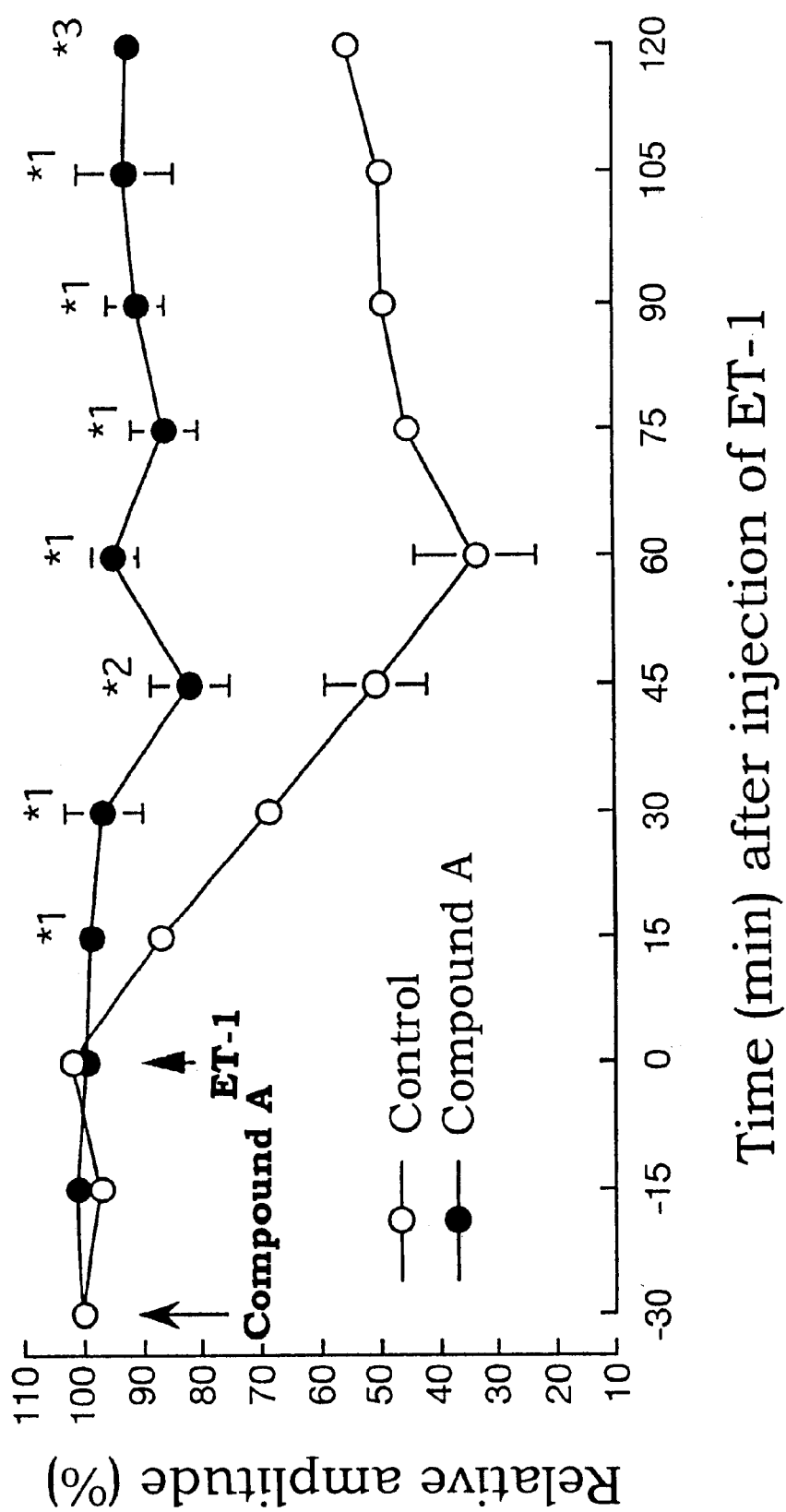
FIG. 9 is a graph showing the time course changes in relative amplitude of VEP upon injection of ET-1 after instillation of a 0.1% ophthalmic solution (containing 0.1% of the compound A of the present invention) in Experimental Example 5, wherein the axis of abscissa shows time (min) when the injection of ET-1 is 0 and the axis of ordinate shows relative amplitude (%). Each value shows mean±standard error (n=3). A significant difference from control is found at each point in time in *1; $P<0.05$,*2; $P<0.01$,*3; $P<0.001$ (paired t-test). The black circle shows instillation of a 0.1% ophthalmic solution and white circle shows instillation of physiological saline.

The effects of the instillation of the 0.1% ophthalmic solution on the attenuation of amplitude of VEP due to ET-1 is shown in FIG. 9. The initial value of amplitude of VEP before instillation was 30.0–76.7. After ET-1 injection, the amplitude of VEP of the eye instilled with physiological saline decreased by 15% as compared to that before injection and decreased by 67% at maximum 60 minutes later. In contrast, the eye instilled with the 0.1% ophthalmic solution showed significant inhibition at any point in time of the attenuation of amplitude of VEP of the eye instilled with physiological saline.

As is evident from the foregoing explanation, the agent for ameliorating ocular circulatory disorder of the present invention increases optic disc blood flow of normal eye particularly by instillation, and inhibits vasocontraction of retinal blood vessel, decease in optic disc blood flow and attenuation of the amplitude of VEP caused by ET-1, without increasing the intraocular pressure. Therefore, the inventive compound is suggested to be effective as a therapeutic agent against, from among the types of glaucoma, particularly normal tension glaucoma caused by ocular circulation disorder and retinitis pigmentosa, macular degeneration, ischemic optic neuropathy, iridocyclitis, retinal artery occlusion, retinal vein occlusion, diabetic retinopathy, ischemic optic neuropathy, choroidal disease following retinal lesion, choroidal disease associated with systemic disease, and the like.

This application is based on application Nos. 285684/1996 and 245559/1997 filed in Japan, the contents of which are incorporated hereinto by reference.

What is claimed is:

1. A method for ameliorating an ocular circulatory disorder caused by a circulatory disorder in the ciliary artery system selected from the group consisting of normal tension glaucoma, retinitis pigmentosa, macular degeneration, ischemic optic neuropathy and iridocyclitis, or for ameliorating an ocular circulatory disorder caused by a circulatory disorder in the central retinal artery system selected from the group consisting of retinal artery occlusion, retinal vein occlusion, diabetic retinopathy, ischemic optic neuropathy, retinal disease following retinal lesion and choroidal disease accompanied by systemic disease, comprising administering a 1,4-dihydropyridine derivative of the formula (I):

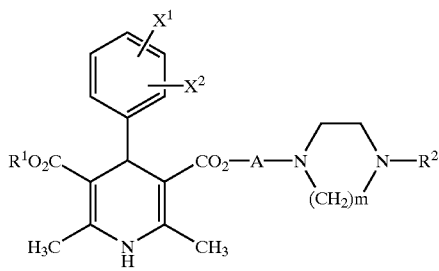

wherein
$X^1$ and $X^2$ are the same or different and each is hydrogen atom or nitro;
$R^1$ is lower alkyl;
$R^2$ is alkenyl;
A is alkylene having a carbon atom bonded with two alkyl and having a total number of carbon atoms of 5 to 10; and
m is 2, or an acid addition salt thereof, in an amount effective for ameliorating the ocular circulation disorder, to a local site in the eye.

2. The method for ameliorating the ocular circulation disorder of claim 1.

3. The method for ameliorating the ocular circulation disorder of claim 1, comprising administering the 1,4-dihydropyridine derivative or an acid addition salt thereof in the form of an eye drop.

4. The method for ameliorating the ocular circulation disorder of claim 1, comprising administering the 1,4-dihydropyridine derivative or an acid addition salt thereof in the form of an eye ointment.

5. The method for ameliorating the ocular circulation disorder of claim 1, which is a method for the prophylaxis and treatment of a disease caused by a circulatory disorder in the ciiiary artery system.

6. The method for ameliorating the ocular circulation disorder of claim 5, wherein the disease caused by the circulatory disorder in the ciliary artery system is a disease selected from the group consisting of normal tension glaucoma, retinitis pigmentosa, macular degeneration, ischemic optic neuropathy and iridocyclitis.

7. The method for ameliorating the ocular circulation disorder of claim 1, which is a method for the prophylaxis and treatment of a disease caused by a circulatory disorder of central retinal artery system.

8. The method for ameliorating the ocular circulation disorder of claim 7, wherein the disease caused by the circulatory disorder in the central retinal artery system is a disease selected from the group consisting of retinal artery occlusion, retinal vein occlusion, diabetic retinopathy, ischemic optic neuropathy, choroidal disease following retinal lesion and choroidal disease accompanied by systemic disease.

9. A method for ameliorating normal tension glaucoma caused by a circulatory disorder in the ciliary artery system, which method comprises administering a 1,4-dihydropyridine derivative of the formula (II):

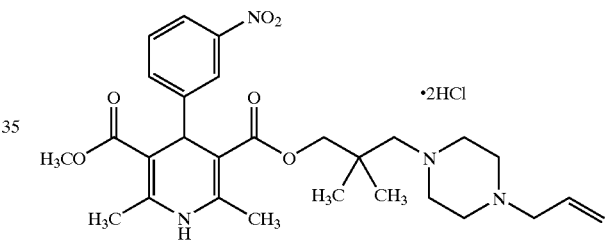

in an amount effective for ameliorating the ocular circulation disorder, to a local site in the eye.

10. The method for ameliorating normal tension glaucoma according to claim 9, comprising administering the 1,4-dihydropyridine derivative in the form of an eye drop.

11. The method for ameliorating normal tension glaucoma according to claim 9, comprising administering the 1,4-dihydropyridine derivative in the form of an eye ointment.

12. A method for increasing blood flow in an optic disc, comprising administering a 1,4-dihydropyridine derivative of the formula (I):

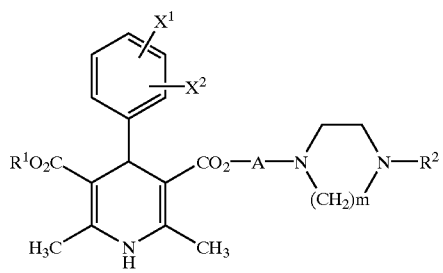

wherein
$X^1$ and $X^2$ are the same or different and each is hydrogen atom or nitro;

$R^1$ is lower alkyl;

$R^2$ is alkenyl;

A is alkylene having a carbon atom bonded with two alkyl and having a total number of carbon atoms of 5 to 10; and m is 2, or an acid addition salt thereof, in an amount effective for increasing blood flow in the optic disc, to a local site in the eye.

13. The method of claim 12, wherein the 1,4-dihydropyridine derivative is administered to the local site in the eye of a subject suffering from an ocular circulatory disorder caused by a circulatory disorder in the ciliary artery system selected from the group consisting of normal tension-glaucoma, retinitis pigmentosa, macular degeneration, ischemic optic neuropathy and iridocyclitis, or an ocular circulatory disorder caused by a circulatory disorder in the central retinal artery system selected from the group consisting of retinal artery occlusion, retinal vein occlusion, diabetic retinopathy, ischemic optic neuropathy, retinal disease following retinal lesion and choroidal disease accompanied by systemic disease.

* * * * *

UNITED STATES PATENT AND TRADEMARK OFFICE
CERTIFICATE OF CORRECTION

PATENT NO. : 6,451,799 B1
DATED : September 17, 2002
INVENTOR(S) : Takahiro Ogawa et al.

It is certified that error appears in the above-identified patent and that said Letters Patent is hereby corrected as shown below:

Column 19,
Lines 33-34, change "retinal disease following retinal lesion and choroidal disease accompanied by systematic disease" to -- choroidal disease following retinal lesion and retinochoroidal disease accompanied by systematic disease --.
Line 61, after "claim 1" insert -- wherein a compound capable of decreasing the intraocular pressure is concurrently administered --.

Column 20,
Line 6, change "ciiiary" to -- ciliary --.
Line 23, change "and choroidal" to -- and retinochoroidal --.

Column 22,
Line 9, change "retinal disease following retinal lesion and choroidal disease accompanied by systematic disease" to -- choroidal disease following retinal lesion and retinochoroidal disease accompanied by systematic disease --.

Signed and Sealed this

Twentieth Day of May, 2003

JAMES E. ROGAN
*Director of the United States Patent and Trademark Office*